(12) United States Patent
Yamaguchi et al.

(10) Patent No.: US 9,075,030 B2
(45) Date of Patent: Jul. 7, 2015

(54) AUTOMATIC ANALYZER

(75) Inventors: Takuya Yamaguchi, Hitachinaka (JP); Shigeki Matsubara, Hitachinaka (JP)

(73) Assignee: HITACHI HIGH-TECHNOLOGIES CORPORATION, Tokyo (JP)

( * ) Notice: Subject to any disclaimer, the term of this patent is extended or adjusted under 35 U.S.C. 154(b) by 694 days.

(21) Appl. No.: 12/993,147

(22) PCT Filed: Apr. 21, 2009

(86) PCT No.: PCT/JP2009/057936
§ 371 (c)(1),
(2), (4) Date: Dec. 14, 2010

(87) PCT Pub. No.: WO2009/142087
PCT Pub. Date: Nov. 26, 2009

(65) Prior Publication Data
US 2011/0090066 A1   Apr. 21, 2011

(30) Foreign Application Priority Data
May 22, 2008   (JP) .................................. 2008-134621

(51) Int. Cl.
*H04Q 5/22* (2006.01)
*G01N 35/00* (2006.01)

(52) U.S. Cl.
CPC .... *G01N 35/00663* (2013.01); *G01N 35/00693* (2013.01); *G01N 35/00712* (2013.01); *G01N 2035/00673* (2013.01); *G01N 2035/00782* (2013.01)

(58) Field of Classification Search
CPC ................................................. G01N 35/00663
USPC ............................... 340/10.51, 500, 501, 514
See application file for complete search history.

(56) References Cited

U.S. PATENT DOCUMENTS

| | | | |
|---|---|---|---|
| 5,663,545 A * | 9/1997 | Marquiss ....................... 235/375 |
| 6,080,364 A | 6/2000 | Mimura et al. |
| 6,275,150 B1 * | 8/2001 | Mandler et al. ............... 340/525 |
| 6,719,203 B2 * | 4/2004 | Hirono et al. ............ 235/462.13 |
| 6,832,722 B1 * | 12/2004 | Cocola et al. .................. 235/385 |
| 7,091,864 B2 * | 8/2006 | Veitch et al. ................ 340/572.8 |
| 2006/0157549 A1 * | 7/2006 | Stein ............................. 235/375 |
| 2007/0072299 A1 * | 3/2007 | Orihashi et al. ................ 436/43 |
| 2007/0237678 A1 * | 10/2007 | Roesicke et al. ........... 422/82.01 |
| 2007/0255756 A1 * | 11/2007 | Satomura et al. ........... 707/104.1 |
| 2008/0024301 A1 * | 1/2008 | Fritchie et al. ............. 340/572.1 |
| 2008/0159914 A1 * | 7/2008 | Ohashi et al. ................ 422/68.1 |
| 2008/0240988 A1 * | 10/2008 | Wakamiya et al. .......... 422/68.1 |
| 2009/0129987 A1 * | 5/2009 | Tanimoto et al. ............. 422/102 |

FOREIGN PATENT DOCUMENTS

| EP | 1 895 305 A1 | 3/2008 |
|---|---|---|
| JP | 10-339732 A | 12/1998 |
| JP | 2003-315343 A | 11/2003 |

(Continued)

*Primary Examiner* — Naomi Small
(74) *Attorney, Agent, or Firm* — Mattingly & Malur, PC

(57) ABSTRACT

An automatic analyzer restartable within a short time includes at least one of quality control information and calibration information stored into an analyzer processing unit. A reagent management unit reads out information from a reagent vessel ID tag affixed to a reagent vessel inside a reagent accommodation unit containing the reagent, and writes information onto the reagent vessel ID tag. The analyzer processing unit uses the reagent management unit to write the quality control information or the calibration information onto the reagent vessel ID tag.

7 Claims, 3 Drawing Sheets

(56) References Cited

FOREIGN PATENT DOCUMENTS

| | | |
|---|---|---|
| JP | 2005-10115 A | 1/2005 |
| JP | 2007-78375 A | 3/2007 |
| JP | 2007-187446 A | 7/2007 |
| JP | 2007-322326 A | 12/2007 |
| WO | 2006/009251 A1 | 1/2006 |
| WO | 2006/123660 A1 | 11/2006 |

* cited by examiner

AUTOMATIC ANALYZER

TECHNICAL FIELD

The present invention relates generally to automatic analyzers for analyzing constituents of biologically derived samples, and more particularly to an automatic analyzer having features and characteristics about a manner of retaining reagent information.

BACKGROUND ART

In automatic analyzers that analyze biologically derived samples, ID information for identifying a reagent to be used for analysis is assigned to reagent vessels on a reagent-specific basis by labeling, tagging, or the like. The analyzer reads the ID information to discriminate for what assay items the reagents are to be used. Identification labels that use bar codes are traditionally known (refer to Patent Document 1, for example).

PRIOR ART DOCUMENTS

Patent Documents

Patent Document 1: JP-2005-10115-A

SUMMARY OF THE INVENTION

Problems to be Solved by the Invention

Bar codes have such advantages as of easy and inexpensive creation of labels. Using the bar codes, however, poses the problems of unreadability, misreading, and the like, since the labels become dirty or moisture remains on the surface of the label.

In addition, the bar codes, once created and affixed to the reagent vessel, cannot be updated, so that only information that has been specified during the manufacture of the reagent can be written in the bar code as the ID information.

Meanwhile, calibration result information and assay result information on a quality control sample are commonly stored in a storage device provided in the automatic analyzer itself. A hard-disk drive (HDD) or the like is used as the storage device. For example, if the machine cycle time of the automatic analyzer is 1.8 seconds, the analyzer repeats data read/write access to the HDD as frequently as every 1.8 seconds, thus shortening the life of the HDD. For example, if the calibration result information or quality control sample assay result information stored within the HDD is lost by the occurrence of HDD trouble, a need arises to again execute the calibration or the assay of the quality control sample. In automatic analyzers of recent years, analytical items have increased and the number of kinds of reagents used has also increased to 70, for example. It took several hours to complete the calibration for the large number of kinds of reagents, and it took much time before restarting of the automatic analyzer.

An object of the present invention is to provide an automatic analyzer restartable within a short time even in case of trouble with a storage device.

Means for Solving the Problems (1) In order to attain the above object, an automatic analyzer according to an aspect of the present invention includes an analyzer processing unit that stores at least one of quality control information and calibration information, the quality control information including reagent-based assay results on an quality control sample, an assay date/time of the quality control sample, and information on analyzer used for the quality control, and the calibration information including reagent-based calibration results, an execution date/time of the calibration, and information on analyzer used for the calibration, wherein the automatic analyzer comprises a reagent management unit that reads out information from a reagent vessel ID tag affixed to a reagent vessel, the reagent vessel being housed in a reagent accommodation unit containing the reagent, and writes the information onto the reagent vessel ID tag, and wherein the analyzer processing unit uses the reagent management unit to write the quality control information or the calibration information onto the reagent vessel ID tag.

The above configuration allows the analyzer to be restarted within a short time even in case of trouble with a storage device.

(2) The automatic analyzer in above item (1) preferably the reagent management unit may read the quality control information that has been written onto the reagent vessel ID tag, and the automatic analyzer further may include display means to display the read quality control information.

(3) The automatic analyzer in item (1) may be preferably constructed so that the reagent management unit reads the quality control information that has been written onto the reagent vessel ID tag, and so that the analyzer processing unit determines from the read quality control information whether the calibration is to be executed.

(4) The automatic analyzer in item (3) preferably may further include display means to display a determination result that the analyzer processing unit draws about whether the calibration is to be executed.

(5) The automatic analyzer in above item (1) may preferably use the reagent management unit to read the calibration information that has been written onto the reagent vessel ID tag, and further includes display means to display the read calibration information.

(6) The automatic analyzer in item (1) may be preferably constructed so that the reagent management unit reads the calibration information that has been written onto the reagent vessel ID tag, and so that when the read calibration information is calibration results obtained during the automatic analysis, the analyzer processing unit applies the calibration results to computing concentrations during analysis of samples.

(7) The automatic analyzer in item (5) may preferably further include display means to display a determination result that the analyzer processing unit draws about whether the calibration is to be executed.

(8) In the automatic analyzer of item (5), the reagent management unit may preferably read the calibration information that has been written onto the reagent vessel ID tag, and the analyzer processing unit may preferably include calibration means adapted to measure calibration data automatically when the read calibration information is calibration results that were obtained earlier than an elapsed definite time period.

Effects of the Invention

In accordance with the present invention, the automatic analyzer is restarted within a short time even in case of trouble with a storage device.

MODE FOR CARRYING OUT THE INVENTION

Hereunder, the configuration and operation of an automatic analyzer according to an embodiment of the present invention will be described with reference to FIGS. 1 to 4.

First, the overall configuration of the automatic analyzer according to the present embodiment will be described using FIG. 1.

Figure 1:
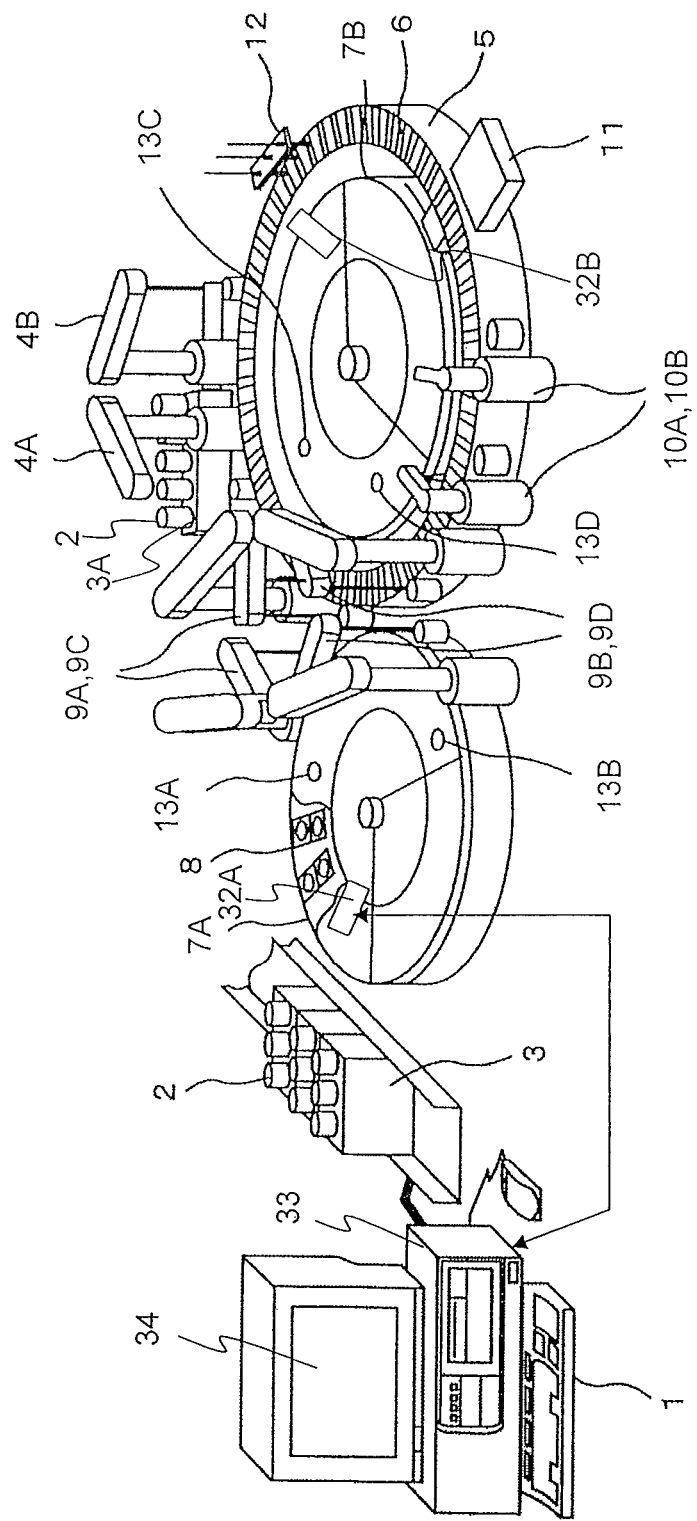
FIG. 1 is a system configuration diagram that shows the overall configuration of an automatic analyzer according to an embodiment of the present invention.

FIG. 1 is a system configuration diagram that shows the overall configuration of the automatic analyzer according to the embodiment of the present invention.

Sample vessels 2 each containing a sample to be assayed are arranged in a transport rack 3. The transport rack 3 is carried to a location of a transport rack 3A present near sample dispensers 4A and 4B. A reaction disk 5 contains a plurality of reaction vessels 6. Under instructions from an operating unit 1, the sample dispensers 4A and 4B each aspirate one of the samples to be assayed, from the sample vessel 2 containing the sample and arranged in the transport rack 3A, and dispense the aspirated sample into the reaction vessels 6. The reaction disk 5 can be pivoted in a circumferential direction. The two sample dispensers, 4A and 4B, are equipped to improve throughput per unit time.

The present embodiment includes two reagent accommodation units, 7A and 7B. Each of the reagent accommodation units 7A and 7B has a cold storage compartment formed internally thereof to retain a plurality of reagent vessels 8 in a cold state. Each reagent vessel 8 holds a specific kind of reagent. Each reagent accommodation units 7A and 7B also has a cover or lid on an upper section thereof, with reagent-aspirating openings 13A and 13B, and 13C and 13D being formed partly in the cover or the lid. Two reagent dispensers 9A and 9B, are present near the reagent accommodation unit 7A. In addition, two reagent dispensers 9C and 9D are present near the reagent accommodation unit 7B. The reagent accommodation unit 7A further has a reagent information management unit 32A thereon. Likewise, the reagent accommodation unit 7B further has a reagent information management unit 32B thereon. A reagent vessel tag from/onto which, as will be described later herein using FIG. 2, information can be read/written using radio waves or electromagnetic waves, is affixed to the reagent vessel 8. The reagent vessel tag is, for example, a radio-frequency identification (RFID) tag. The reagent information management unit 32A and 32B each reads out the information relating to the reagent, from the reagent vessel tag, or writes the information onto the tag.

The reaction vessels 6 into which the sample to be assayed has been dispensed by the sample dispenser 4A and 4B, each can be moved to a position for the reagent dispenser 9A and 9B, and 9C and 9D to dispense the reagent, by pivoting the reaction disk 5. The reagent accommodation units 7A and 7B each can also be pivoted, but the cover or lid thereof does not turn. Pivoting the reagent accommodation units 7A and 7B allows a predetermined reagent to be positioned under any one of the openings 13A and 13B or the openings 13C and 13D, respectively. The reagent dispenser 9A aspirates the predetermined reagent via the opening 13A and dispenses the aspirated reagent into one of the reaction vessels 6 into which the sample to be assayed was dispensed. Additionally, the reagent dispenser 9B aspirates the predetermined reagent via the opening 13B and dispenses the aspirated reagent into another reaction vessel 6 into which the sample to be assayed has already been dispensed. Likewise, the reagent dispenser 9C aspirates the predetermined reagent via the opening 13C and dispenses the aspirated reagent into yet another reaction vessel 6 into which the sample to be assayed has been dispensed. Furthermore, the reagent dispenser 9D aspirates the predetermined reagent via the opening 13D and dispenses the aspirated reagent into a further reaction vessel 6 into which the sample to be assayed has been dispensed.

Each reaction vessel 6 containing the dispensed sample and reagent is moved to a location of a stirrer 10A or 10B, where the two substances are then stirred for mixing. There will be a need to use one, two, three, or more kinds of reagents, depending upon an assay item. Necessary kinds of reagents may therefore be sequentially aspirated using the reagent dispensers 9A to 9D, then dispensed into the reaction vessel, and stirred for mixing.

Upon an elapse of a predetermined reaction time following the mixing of the sample and the reagent, the reaction vessel 6 is moved to a location of a photometer 11. The photometer 11 includes a light source lamp, a diffraction grating that divides light, and a photodetector. The photometer 11 is used to perform photometrical analyses on a color-developing property of chemical reactions of the sample.

After the analyses, the reaction vessel 6 is washed by a washer 12 to prepare for analysis of a next sample. A sample to be analyzed is aspirated and then the transport rack 3 with that sample vessel 2 disposed therein is unloaded from an analyzing section.

In addition, under instructions from the operating unit 1, reagent vessels 8 are each moved to locations of the reagent information management units 32A and 32B, where specific reagent information for each reagent vessel 8 is then read out from or written onto the respective reagent vessel tags.

Next, the configuration of a reagent vessel used in the automatic analyzer according to the present embodiment is described below using FIG. 2.

Figure 2:
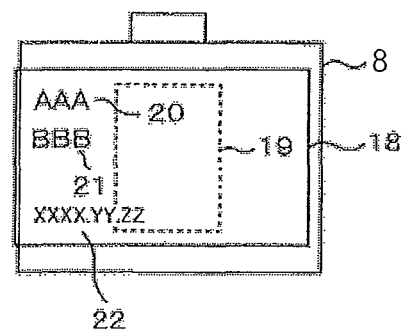
FIG. 2 is a front view of a reagent vessel, showing the configuration of the reagent vessel used in the automatic analyzer according to the embodiment of the present invention.

FIG. 2 is a front view of a reagent vessel, showing the configuration of the reagent vessel used in the automatic analyzer according to the embodiment of the present invention.

Each reagent vessel 8 disposed in the reagent accommodation unit 7 has an attached label 18 for visual identification information on the reagent contained in the reagent vessel. A reagent vessel tag from or onto which the information is to be read out or written using radio waves or electromagnetic waves is buried in the label 18. The label 18 on the reagent vessel allows visual confirmation of the reagent's manufacturer name 20, applicable assay item name 21, expiration date, and other information that usually remains unchanged from a manufacturing date of the reagent. The same information is written on the reagent vessel tag 19. Assay results on quality control samples, as well as calibration results, are also written on the reagent vessel tag 19. The calibration results and the assay results will be described later herein.

The analyzer uses a reagent to analyze one or a plurality of samples (calibrators) of a known concentration, then creates a calibration curve from data representing a concentration-absorbance relationship, and acquires data for calibrating measured data. This sequence is called calibration. The analyzer also outputs analytical results on general samples, based upon the calibration-acquired data relating to the concentration-absorbance relationship. The calibration is conducted to correct an instrumental error of the analyzer with respect to data measurements on general samples, differences between reagent lots, and the like. Results of the calibration, execution time of the calibration, an ID of the analyzer which has conducted the calibration, and the like are written onto the reagent vessel tag 19. In addition, the same information is stored into an internal storage unit of the analyzer processing unit 33 shown in FIG. 1, such as an HDD.

Furthermore, quality control samples that were manufactured in a regulated reference concentration range are periodically assayed to confirm normality of measured-data calibration, that is, stability of the measured data. Assay results on each quality control sample, execution time of quality control, the ID of the analyzer which has conducted quality control, and other information are written onto the reagent vessel tag 19. Moreover, the same information is stored into the internal storage unit of the analyzer processing unit 33, such as the HDD.

Commonly, calibration precedes a start of analysis and is followed by the assay of a quality control sample to confirm that the analyzer and the reagent are already conditioned for normal (proper) analysis. After the confirmation, the analysis of general samples is started. If the quality control data range is overstepped at this time, necessary corrective actions such as replacing the reagent and/or readjusting the analyzer are taken before the calibration and the assay of quality control samples are both repeated once again. After this, the analyzer continues the analysis of general samples while periodically assaying the quality control samples and confirming normal reagent and analyzer states. If the measurement results that have been obtained during the periodic assay of the quality control samples are outside the quality control data range, recalibration takes place and re-analysis of the quality control samples follows for the reconfirmation of the reagent and analyzer states.

Next, reading/writing information from/onto a reagent vessel tag in the automatic analyzer according to the present embodiment is described below using FIG. 3.

Figure 3:
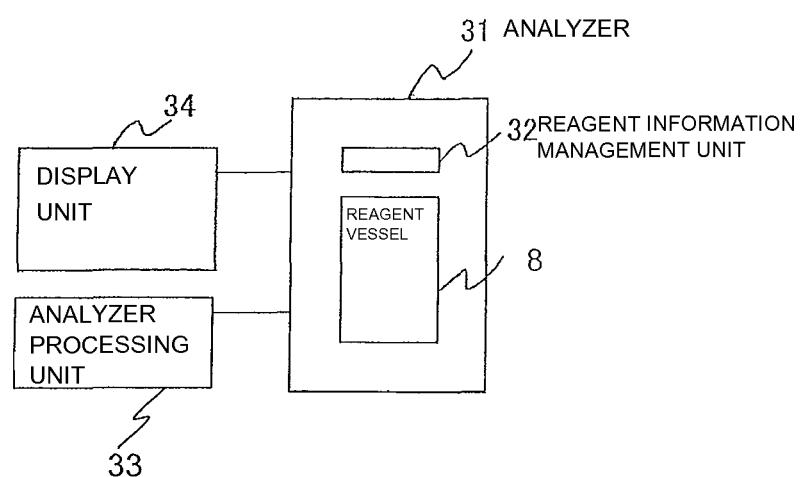
FIG. 3 is a block diagram that shows the configuration of constituent elements for reading/writing information from/onto a reagent vessel tag in the automatic analyzer according to the embodiment of the present invention.

FIG. 3 is a block diagram that shows the configuration of constituent elements for reading/writing information from/onto a reagent vessel tag in the automatic analyzer according to the embodiment of the present invention.

Before, during, or after the analysis of an quality control sample with the analyzer 31, each reagent vessel 8 is moved to the location of the reagent information management unit 32 that writes information onto the reagent vessel tag. Next, the reagent information management unit 32 on the reagent accommodation unit 7 writes the assay results relating to the quality control sample, the analyzer ID such as a serial number, and the assay date/time of the quality control sample, onto the reagent vessel tag attached to the reagent vessel 8 containing the reagent which has been used for quality control. Additionally, the same information is stored into the internal storage unit of the analyzer processing unit 33, such as the HDD.

Quality control information that the reagent management unit 32 has read out can also be displayed on a display unit 34 of the analyzer. Thus, a user can confirm the quality control information relating to any necessary reagent, and save or print out data.

The movement of each reagent vessel 8 to the location of the reagent information management unit 32 that writes information onto the reagent vessel tag is also conducted before, during, or after calibrator analysis with the analyzer 31. Next, the reagent information management unit 32 on the reagent accommodation unit 7 writes the assay results relating to the calibrator, the analyzer ID such as the serial number, and the assay date/time of the calibrator, onto the reagent vessel tag attached to the reagent vessel 8 containing the reagent which has been used for the calibration. Additionally, the same information is stored into the internal storage unit of the analyzer processing unit 33, such as the HDD.

Calibration information that the reagent management unit 32 has read out can also be displayed on the display unit 34 of the analyzer. Thus, the user can confirm the calibration information relating to any necessary reagent, and print out or save data.

Traditionally, quality control information and calibration information have only been stored into an internal storage unit, such as HDD, of an analyzer processing unit. The present embodiment, however, writes the two kinds of information into the reagent vessel tag of the reagent vessel. Consequently, even if HDD trouble results in a loss of the calibration result information and/or quality control sample assay result information stored within the HDD, the user can reuse the information that has been written onto the reagent vessel tag, without re-executing the calibration or re-assaying the quality control sample. That is to say, recalibration is unnecessary and the automatic analyzer can be restarted within a short time.

Next, an analytical method using reagent vessel information in the automatic analyzer according to the present embodiment is described below using FIG. 4.

Figure 4:
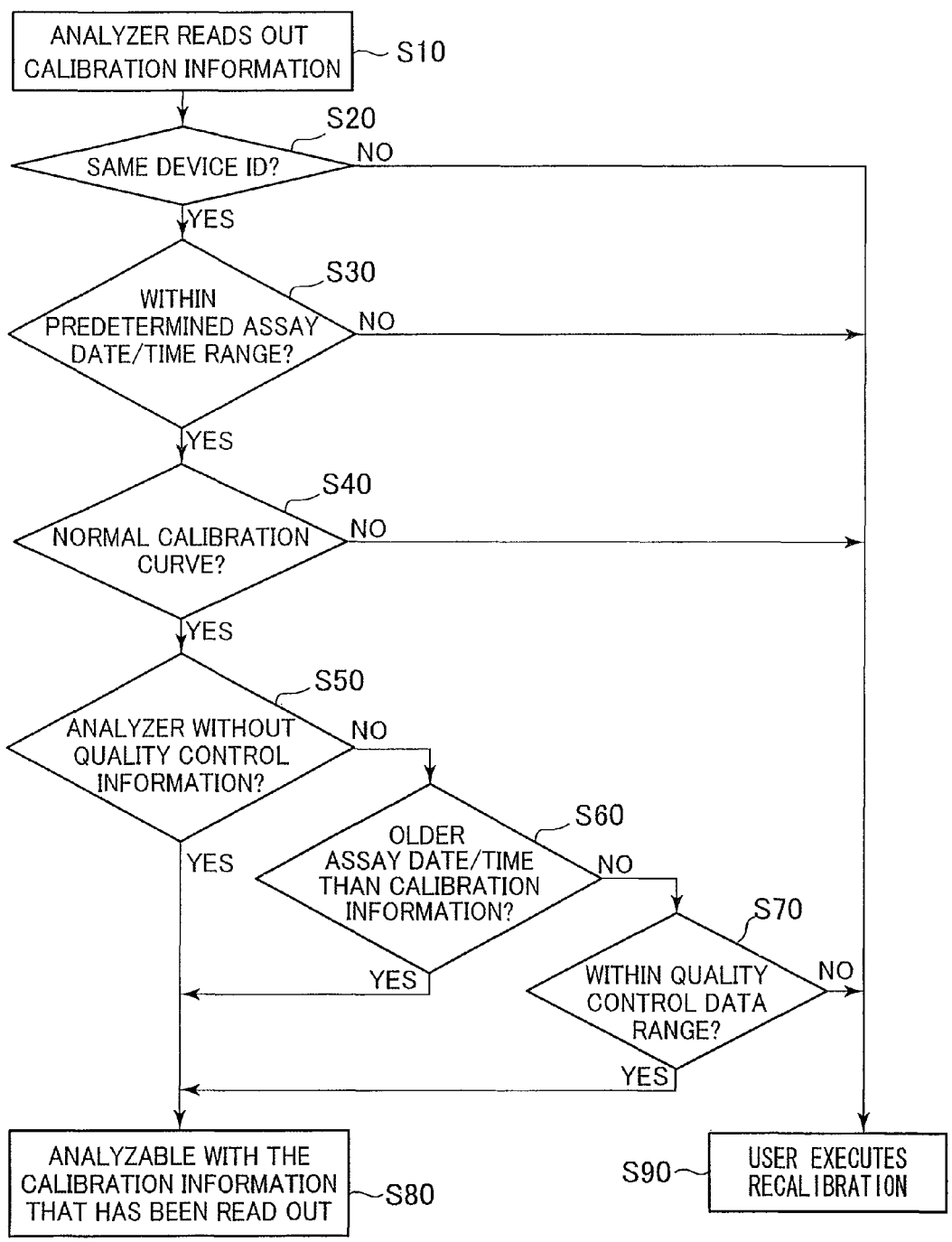
FIG. 4 is a flowchart that shows an analytical method using reagent vessel information in the automatic analyzer according to the embodiment of the present invention.

FIG. 4 is a flowchart that shows the analytical method using reagent vessel information in the automatic analyzer according to the embodiment of the present invention.

In step S10, the analyzer processing unit 33 uses the reagent management unit 32 to read out calibration information from the reagent vessel tags on reagent vessels.

Next, in step S20, the analyzer processing unit 33 determines whether the device ID in the calibration information which has been read out differs from the device ID of the analyzer. When the device ID in the information differs from that of the analyzer, the analyzer processing unit 33 automatically displays a message on the display unit 34 to prompt the user to execute calibration in step S90 using the reagent. This display aids user determination and simplifies operations on the analyzer. In addition, when a calibrator is already set in the analyzer, operations can be further simplified by making the calibrator automatically analyzable without an instruction from the user.

When it is determined in step S20 that the device ID is the same as that of the analyzer, the analyzer processing unit 33 next determines in step S30 whether the assay date/time has already passed a predetermined period. In a case where the predetermined period has been passed, the analyzer processing unit 33 automatically displays a message on the display unit 34 to prompt the user to execute calibration using the reagent.

In step S30, when the predetermined period is determined not to have been passed, the analyzer processing unit 33 next determines in step S40 whether the calibration curve is normal. In a case where the calibration curve is determined to be abnormal, the analyzer processing unit 33 automatically displays a message on the display unit 34 to prompt the user to execute calibration in step S90 using the reagent.

In step S50, the analyzer processing unit 33 checks the above-read quality control information and determines whether the device ID is the same as that of the analyzer. When the device ID is the same as that of the analyzer, the analyzer processing unit 33 determines in step S60 whether the assay date/time of the quality control sample is within the predetermined period. In a case where the assay date/time is within the predetermined period, the analyzer processing unit 33 determines in step S70 whether the assay results stay within the quality control data range. In a case where this range is overstepped, the analyzer processing unit 33 automatically displays a message on the display unit 34 to prompt the user to execute calibration in step S90 using the reagent.

When the analyzer is determined in step S50 to have no quality control information, when the quality control information is determined in step S60 to be older than the predetermined period, or when the quality control data is determined in step S70 to stay within the predetermined range, the analyzer processing unit 33 applies the above-created calibration curve to computing concentrations during analysis of general samples. This allows the analysis of the general samples without recalibration, and hence, reduction in assay time and in calibrator consumption.

It has been described above that calibration information and quality control information are both checked. However, only calibration information may be checked.

Additionally, a history of assay results on the quality control sample can be recorded on a device-specific basis on reagent vessel tags, and the assay results history of the quality control sample that has been read from one specific reagent vessel tag by the analyzer can be displayed on the display unit 34 or printed. Thus, the user can obtain information on a state of the reagent.

Furthermore, for assay item that is to be analyzed with a plurality of reagents, in a case where the plurality of reagents are accommodated in independent reagent vessels and these reagent vessels are used as a pair, one or both of the quality control information and calibration information analyzed using the reagent contained in one of the paired reagent vessels can be written onto the reagent vessel tags of the paired reagent vessels. The information can also be read out from the reagent vessel tag(s) on one of the paired reagent vessels or at least one thereof. The paired reagent vessels can therefore be recognized and the analyses can be conducted using the reagents as a pair.

As described above, according to the present embodiment, the analyzer can be restarted within a short time, even if storage unit trouble occurs.

In addition, analytical operations can be simplified by using the reagent vessels that include ID tags onto which the reagent information generated after the reagent has been manufactured can be written.

Furthermore, if, during the manufacture of a reagent, the manufacturer of the reagent has pre-written a lot number of a calibrator associated with the reagent, a reference curve, and other information, onto the reagent tag affixed to a reagent vessel, the user can display on the display unit 34 or print out the analyzer-based calibration results and the reference curve pre-written on the tag. The user can thus obtain the calibration results and information on a state of the reagent which was used for the calibration.

Besides, if, during the manufacture of a reagent, the manufacturer of the reagent has pre-written the kind of control sample to be assayed using that reagent, a lot number of the reagent, a target value, and other quality control information, onto the reagent tag affixed to a reagent vessel, the user can display on the display unit 34 or print out the analyzer-based quality control sample assay results and the quality control information pre-written on the tag. The user can thus obtain information on a state of the reagent which was used for the assay of the control sample.

Moreover, if a history of all calibration results and quality control information about the reagent is written onto the reagent tag beforehand, this contributes to examining probable causes of any abnormal assay results from comparisons thereof with the historical information.

Besides, the information written on the reagent tag of the reagent vessel may be read out by and displayed on a computer other than the analyzer. This will enable rapid troubleshooting and error cause investigation, irrespective of the user's operations on the analyzer, by reading the reagent tag information with that external computer.

DESCRIPTION OF REFERENCE NUMERALS

1 . . . Analyzer operating unit
2 . . . Sample vessel
3 . . . Transport rack
4 . . . Sample dispenser
5 . . . Reaction disk
6 . . . Reaction vessel
7 . . . Reagent accommodation unit
8 . . . Reagent vessel
9 . . . Reagent dispenser
10 . . . Stirrer
11 . . . Photometer
12 . . . Washer
13 . . . Opening in cold storage compartment
18 . . . Label on reagent vessel
19 . . . Reagent vessel tag
20 . . . Name of manufacturer of reagent
21 . . . Name of assay item applicable to reagent
22 . . . Expiration date of reagent
31 . . . Analyzer
32 . . . Reagent management unit
33 . . . Analyzer processing unit
34 . . . Analyzer display unit

The invention claimed is:

1. An automatic analyzer comprising an analyzer processing unit that stores calibration information including reagent-based calibration results, an execution date/time of the calibration, and information of an analyzer used for the calibration, wherein the automatic analyzer comprises a reagent management unit that reads out information including calibration information from a reagent vessel ID tag affixed to a reagent vessel containing a reagent of a plurality of reagents, the reagent vessel being housed in a reagent accommodation unit, and the reagent management unit writes the information onto the reagent vessel ID tag; and wherein the analyzer processing unit uses the reagent management unit to write the calibration information onto the reagent vessel ID tag, wherein the analyzer processing unit determines whether the information of an analyzer in the calibration information which has been read out from the reagent vessel ID tag differs from that of the automatic analyzer having the analyzer processing unit, determines whether the execution date/time which has been read out from the reagent vessel ID tag has passed a predetermined period, determines whether a calibration curve which has been read out from the reagent vessel ID tag is abnormal, and wherein the analyzer processing unit analyzes samples by using the calibration curve without recalibration when the information of the analyzer is determined to be the same as that of the automatic analyzer having the analyzer processing unit, the execution date/time is determined not to have passed the predetermined period, and the calibration curve is determined to be normal.

2. The automatic analyzer according to claim 1, wherein: the automatic analyzer further comprises display means to display the read calibration information.

3. The automatic analyzer according to claim 1, further comprising: means for displaying a determination result of the analyzer processing unit about whether calibration is to be executed.

4. The automatic analyzer according to claim 1, wherein: the analyzer processing unit includes calibration means adapted to measure calibration data automatically when the read calibration information is calibration results that were obtained earlier than an elapsed definite time period.

5. The automatic analyzer according to claim 1,
wherein the analyzer processing unit stores quality control information which includes reagent-based assay results on a quality control sample, an assay date/time of the quality control sample, and information of an analyzer used for the quality control,
wherein the information read out from the reagent vessel ID tag by the reagent management unit includes quality control information,
wherein the analyzer processing unit uses the reagent management unit to write quality control information onto the reagent vessel ID tag,
wherein the analyzer processing unit determines whether the information of an analyzer in the quality control information which has been read out from the reagent vessel ID tag is the same as the information of the analyzer in the calibration information,
determines whether the assay date/time in the quality control information is within the predetermine period,
determines whether the assay results in the quality control information is within a quality control data range,
wherein the analyzer processing unit displays whether recalibration is necessary or not when the information of the analyzer in the quality control information is determined to be the same as the information of the analyzer in the calibration information, the assay date/time in the quality control information is determined to be within the predetermined period, and the assay results in the quality control information are out of the quality control data range.

6. The automatic analyzer according to claim 1,
wherein the plurality of reagents are accommodated in the independent reagent vessels housed in a reagent accommodation unit and the reagent vessels are paired,
wherein calibration information of the reagent contained in one of the paired reagent vessels is written onto the reagent vessel ID tag of the other of the paired regent vessels and when assay item is to be analyzed with a plurality of reagents, and the reagent vessels are used as a pair,
wherein the paired reagent vessels are recognized and the analyses is conducted using the reagents as a pair by reading out the calibration information from the reagent vessel tag IDs on one of the paired reagent vessels or at least one thereof.

7. The automatic analyzer according to claim 1, wherein a quality control information is pre-written onto the reagent vessel ID tag.

* * * * *